United States Patent [19]

Reis

[11] Patent Number: 4,811,747

[45] Date of Patent: Mar. 14, 1989

[54] ORANGE JUICE HAIR TREATMENT METHOD

[76] Inventor: Virginia H. Reis, 92 Mather Rd., Stamford, Conn. 06903

[21] Appl. No.: 479,675

[22] Filed: Mar. 28, 1983

[51] Int. Cl.$^4$ ............................................... A45D 7/00
[52] U.S. Cl. .......................... 132/203; 252/DIG. 13; 424/70
[58] Field of Search ........................... 132/7, 350–351, 132/368, 602

[56] References Cited

PUBLICATIONS

Balsam/Sagarin, Cosmetics: Science and Technology, vol. 2, May 2, 1975, p. 365.
Cosmetics Science and Technology, Sagarin, 1957, p. 537.
Cosmetics Science and Technology, Second Edition, vol. 2, Balsam & Sagarin, pp. 20–21.
Cosmetics Science & Technology, 2nd Ed., vol. 2, Balsam & Sagarin, pp. 602, 350, & 365.

Primary Examiner—Richard J. Apley
Assistant Examiner—Paul Prebilic
Attorney, Agent, or Firm—Parmelee, Bollinger & Bramblett

[57] ABSTRACT

A method is described for using orange juice in a treatment for hair. Juice is prepared from either fresh oranges or orange juice concentrate and applied to the hair after the hair has been moistened. The hair is then styled before it dries using a styling instrument such as the fingers, a comb or a brush. The setting or holding power of the preparation can be controlled by varying the amounts of orange juice and water that are used.

5 Claims, No Drawings

ORANGE JUICE HAIR TREATMENT METHOD

FIELD OF THE INVENTION

This invention is in the field of hair dressing and grooming and cosmetic treatments.

BACKGROUND OF THE INVENTION

Since the beginning of time man and particularly woman has sought natural ingredients for beneficial purposes in beautifying themselves. These ingredients were used for cosmetic and medicinal purposes. It was not known exactly why they did the good they did, but, although they did not always perform some magic they made that particular person feel good, look good and each person knew what ingredients worked well for them and made the formulation a very personal product.

Nowadays a multitude of hair care products are readily available to the consumer, but, they are often preparations composed of a complexity of ingredients of petroleum derivatives and other complex chemicals, agents and food colorings. These chemicals are often quite expensive to use. The consumer does not always know exactly what ingredients in these preparations might be causing allergies and other adverse reactions and they must be labeled with special instructions and be kept from children and other people to avoid drinking them either accidently or on purpose.

With all the complex chemical formulations helping our high technologic society today there is also an urgency to simplify our lives and make our lives easier and less complicated and to use natural ingredients. In an attempt to economize many people try to imitate and prepare some of these commercial products at home. However, they quite often end up with a gooey homemade brew bubbling and evaporating all over the stovetop and their time consuming painstakingly prepared formula ends up a hopeless mess.

SUMMARY

An object of the present invention is to provide a method of hair dressing using simple, natural, inexpensive and convenient ingredients which helps make hair look neat and attractive and as an extra benefit gives the hair a pleasant fragrance.

Another object of the present invention is to provide a method of setting and styling hair in which the holding power of the preparation can be controlled by varying the amount of water used in the treatment.

Another object of the present invention is to provide a method of conditioning human hair which is easily applied and does not leave the hair feeling sticky or tacky afterwards.

Another objectof the present invention is to provide an easily applied method of treating human hair which when used over a prolonged time of about one year will improve the condition of the said hair.

DETAILED DESCRIPTION

First, juice is extracted from a fresh orange and used either alone or in solution with water. Thawed frozen orange juice concentrate can be used either alone or in solution with water. The concentration of orange juice and water will be a personal decision depending on each person's type of hair and hair style desired.

If fresh oranges are used seedless or California Naval varieties are preferred, since the problem of cleaning up and discarding seeds is avoided.

Next, after the hair has been dampened with water, the juice is applied and rubbed into the hair. The preparation is then allowed to dry partially.

Third, before the hair is completely dry, a styling instrument, such as the fingers, a comb, a brush or the like are used to shape and style the hair in the desired manner. Other hair styling conveniences could also be used at this point such as clips, rollers and the like.

The holding or setting efficacy of the treatment can be varied by using different mixtures of orange juice and water. Increases in the concentration of orange in the water produce concomitant increases in the binding effect of the treatment.

When the desired concentration of orange juice or orange juice and water is foiund there are several convenient ways of storing and using this solution. For example, the personally preferred solution could be strained for added convenience, mixed with or without water and kept in a misting bottle or a squirt type bottle not only for convenience but also to regulate the evenness of the application of the orange juice solution.

The solution, for example, could be frozen in ice cube shapes or other quantity shapes equivalent to a single application and could be defrosted in convenient small amounts without waste. Applicant finds defrosting a tablespoon of frozen orange juice concentrate particularly convenient. This also eliminates the need for preservatives which might be required for other homemade cosmetic preparation.

This invention would be particularly useful when traveling especially in foreign countries where your favorite hair preparation might not be available.

Another example of the use of the present invention is for the styling of dry hair whereby orange juice is employed as a dilute solution and is applied for example by misting onto the dry hair until the hair possesses the desired wetness for proper styling.

Since other changes and modifications varied to fit particular requirements will become understood by those skilled in the art, the present invention is not considered limited to the examples chosen for purposes of illustration, and covers all changes and modifications which do not constitute a departure from the true spirit and scope of this invention as defined in the following claims and reasonable equivalents of the claimed elements.

What is claimed is:

1. A method of setting and holding the set of the hair of a human being without leaving the hair feeling sticky or tacky comprising wetting the hair of said human with water and applying to said hair a hair setting effective amount of the juice of an orange, allowing the hair to partially dry and setting the hair into the desired fashion before the hair dries completely.

2. The method of claim 1 wherein the orange juice is orange juice concentrate.

3. The method of claim 1 wherein the orange juice is first diluted with water before application to the hair.

4. The method of claim 1 wherein the orange juice is orange juice concentrate and is first diluted with water before application to the hair.

5. A method of setting and holding the set of the hair of a human being without leaving the hair feeling sticky or tacky comprising applying to said hair a hair setting effective amount of a dilute solution of orange juice onto dry human hair until the hair possesses the desired wetness for setting and styling or shaping said hair into the desired fashion before the hair dries completely.

* * * * *